United States Patent
Nordbruch

(10) Patent No.: US 9,108,592 B2
(45) Date of Patent: Aug. 18, 2015

(54) METHOD FOR OPERATING A VEHICLE

(71) Applicant: Stefan Nordbruch, Kornwestheim (DE)

(72) Inventor: Stefan Nordbruch, Kornwestheim (DE)

(73) Assignee: ROBERT BOSCH GMBH, Stuttgart (DE)

( * ) Notice: Subject to any disclaimer, the term of this patent is extended or adjusted under 35 U.S.C. 154(b) by 11 days.

(21) Appl. No.: 13/737,193

(22) Filed: Jan. 9, 2013

(65) Prior Publication Data
US 2013/0179024 A1 Jul. 11, 2013

(30) Foreign Application Priority Data
Jan. 9, 2012 (DE) .......................... 10 2012 200 189

(51) Int. Cl.
| | |
|---|---|
| *B60W 50/08* | (2012.01) |
| *B60W 50/12* | (2012.01) |
| *B60W 50/14* | (2012.01) |
| *A61B 5/18* | (2006.01) |
| *B60R 99/00* | (2009.01) |
| *B60K 28/06* | (2006.01) |
| *G08B 21/02* | (2006.01) |
| *A61B 5/00* | (2006.01) |

(52) U.S. Cl.
CPC . *B60R 99/00* (2013.01); *A61B 5/18* (2013.01); *B60K 28/06* (2013.01); *G08B 21/02* (2013.01); *A61B 5/4836* (2013.01); *A61B 2560/0266* (2013.01)

(58) Field of Classification Search
USPC .............. 701/36, 41, 45, 93, 96, 23; 340/500, 340/463, 466–7, 901–904, 576
See application file for complete search history.

(56) References Cited

U.S. PATENT DOCUMENTS

| | | | | |
|---|---|---|---|---|
| 3,780,311 | A * | 12/1973 | Brown | 307/10.6 |
| 4,926,164 | A * | 5/1990 | Porter et al. | 340/576 |
| 5,396,215 | A * | 3/1995 | Hinkle | 340/426.17 |
| 6,060,989 | A * | 5/2000 | Gehlot | 340/576 |
| 6,271,746 | B1* | 8/2001 | Lisiak et al. | 340/425.5 |
| 6,748,792 | B1* | 6/2004 | Freund et al. | 73/23.3 |
| 6,920,389 | B1* | 7/2005 | Hale et al. | 701/115 |
| 7,911,350 | B2* | 3/2011 | Shoji et al. | 340/576 |
| 2005/0200201 | A1* | 9/2005 | Jabaji et al. | 307/10.1 |
| 2006/0001531 | A1* | 1/2006 | Waterman | 340/438 |
| 2006/0036358 | A1* | 2/2006 | Hale et al. | 701/45 |
| 2010/0295707 | A1* | 11/2010 | Bennie et al. | 340/988 |
| 2013/0093603 | A1* | 4/2013 | Tschirhart et al. | 340/902 |

FOREIGN PATENT DOCUMENTS

DE 100 42 367 A 5/2002

* cited by examiner

*Primary Examiner* — Yonel Beaulieu
(74) *Attorney, Agent, or Firm* — Kenyon & Kenyon LLP

(57) ABSTRACT

A method for operating a vehicle includes checking a state of health of the driver during operation of the vehicle, in particular when it is started, and starting a safety program for operating the vehicle when a predefined state of health is detected.

19 Claims, 2 Drawing Sheets

METHOD FOR OPERATING A VEHICLE

CROSS REFERENCE TO RELATED APPLICATION

The present application claims priority to Application No. DE 10 2012 200 189.1, filed in the Federal Republic of Germany on Jan. 9, 2012, which is incorporated herein in its entirety by reference thereto.

FIELD OF INVENTION

The present invention relates to a method for operating a vehicle, a system for checking the state of health of a driver, a mobile device and a data memory.

BACKGROUND INFORMATION

It is known in the related art to detect a driver's attention and fatigue while driving a vehicle. An appropriate system is described in Germany Application No. DE 100 42 36 7 A.

SUMMARY

An object of the present invention is to provide an improved method for operating a vehicle.

One advantage of the method described here is that the driver's state of health is checked in particular when the vehicle is being started. When a predefined poor state of health is detected, a safety program for operating a vehicle is started. This prevents a driver in a poor state of health from operating the vehicle. This also prevents an accident from happening because the driver is in an acute poor state of health. To prevent an accident, a safety program is started in order to operate the vehicle at least in a partial function when a poor state of health is detected. This object is also achieved in that a system for checking the driver's state of health is kept ready in the vehicle.

In addition, this object is achieved in that a mobile device in the vehicle is used which keeps data ready, in particular a reference value for checking on the driver's state of health. Additional advantageous exemplary embodiments of the present invention are also described.

In one exemplary embodiment, the driver's state of health is checked at predefined time intervals, in particular regularly, during operation of the vehicle. The safety program is started when a predefined poor state of health is detected. By checking regularly, there is assurance that a sudden occurrence of a poor state of health, for example a heart attack or a blackout, even while the vehicle is being driven, will not result in an accident.

In another exemplary embodiment, the safety program carries out at least one of the following functions: outputting a warning signal, informing other road users, in particular vehicles, starting an automatic driving function, in particular automatic parking of the vehicle, limiting a function of the vehicle, for example, the speed, and suppressing operation of the vehicle. Suppressing the operation of the vehicle is possible when starting the vehicle in particular.

The safety program is able to reduce the probability of an accident with the aid of the functions described here. One or more functions may be taken over by the safety program, depending on the driver's state of health. For example, if it is found that the driver is in a poor state of health, but which may not result in an acute hazard, then it is sufficient to merely output a warning signal, for example. However, if a heart attack is detected, for example, then the safety program should either suppress operation of the vehicle or should completely take over the guidance of the vehicle, if the driving situation allows, and automatically stop the vehicle at the side of the road.

In another exemplary embodiment, a reference value, in particular a result from a previous check, is taken into account in evaluating the driver's heath condition. A fast and simple detection of a predefined poor state of health is possible by using the reference value. By taking into account a result of a previous check, a more accurate conclusion about a deterioration of the state of health may be made. Thus the driver's poor state of health is detected quickly and precisely. In addition, by using the results of previous checks, individual states of health, in particular the driver's medical history, may be taken into account. Intervention into the operation of the vehicle by the safety program may thus be limited to situations which are actually necessary.

In another exemplary embodiment, the result of the check of the state of health is either saved in a memory in the vehicle or the data is transferred to an external memory. This saving step makes it possible to check on whether the driver's state of health was responsible for an accident after it has occurred, for example. Furthermore, the driver's state of health may be checked in greater detail in a hospital due to the transfer to an external memory. For example, the driver's state of health may be transmitted to a hospital which has access to additional data about the driver's state of health, in particular medical files. Complex and accurate checks of the driver's state of health may be carried out in the hospital. In addition, information about the actual state of health of a driver may be transmitted from an external computer unit. For example, an all-clear message or an immediate start of the safety program, in particular a certain function, may be transmitted to the vehicle from an external source. The function to be started is defined depending on the state of health.

In another exemplary embodiment, the memory used is a mobile memory in the vehicle, for example, a memory of a communication device, in particular a computer or a mobile telephone. This provides increased flexibility in storage of the data. In particular the data may be picked up after the end of the trip and analyzed further at home or in a hospital.

In another exemplary embodiment, the data or the reference value for the driver's state of health are/is received from an external database. These data may be provided by a hospital, for example, which has more detailed data about the driver's state of health, in particular a maintained medical file.

The safety program may also have the function that information about the driver's state of health is transmitted to an external computer unit, in particular to a hospital or a physician. An emergency physician may thus be contacted automatically if the driver's state of health is very poor.

In another exemplary embodiment, after the predefined poor state of health has been detected, corresponding information is transmitted to other road users, in particular to other vehicles. This information may have as its content, for example, "Caution, accident" or "Please assist". Consequences of an occurring accident on other road users may be limited in this way.

The present invention is explained in greater detail below with reference to the accompanying drawings.

DETAILED DESCRIPTION

Figure 1:
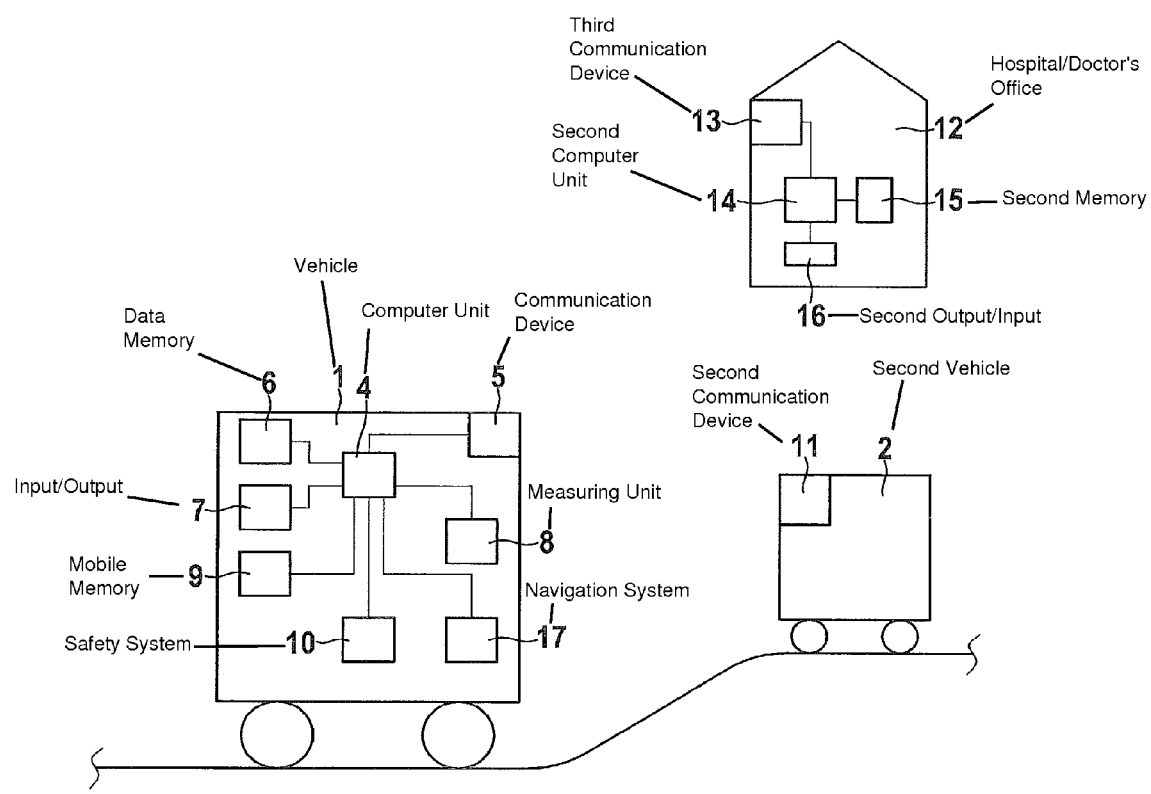
FIG. 1 shows a schematic depiction of a vehicle, another vehicle and a hospital.

FIG. 1 shows in a schematic depiction a driving situation involving a vehicle 1, a second vehicle 2 and an external stationary computer unit 14, which is located in a hospital or a doctor's office, for example. Vehicle 1 has a computer unit 4, which is connected to a communication device 5, a data memory 6, an input/output 7 and a measuring unit 8. Furthermore, computer unit 4 may be connected to a mobile memory 9, which may be part of a computer or a mobile telephone, for example. Depending on the specific, exemplary embodiment selected, permanently installed memory 6 may be omitted if mobile memory 9 is present.

Input/output 7 is used for input of data and for output of data information to the driver. Measuring unit 8 monitors the driver's state of health. For example, the driver's body temperature, pulse rate, blood pressure and other measured physiological values and functions may be detected, which permit a statement about the driver's state of health. With the aid of communication device 5, data and information may be transmitted from vehicle 1 and received by vehicle 1. For example, data about the driver's state of health, in particular a reference value for checking the driver's state of health, are saved in memory 6 or in mobile memory 9.

In addition, computer unit 4 is connected to a safety system 10. Safety system 10 may be designed as a driver assistance system, for example. Furthermore, safety system 10 may be designed in the form of a computer unit on which a safety program capable of executing at least one of the following functions is running: outputting a warning signal via input/output 7, outputting a warning signal to other road users and/or to external computer unit 14 with the aid of communication device 5. The warning signal may contain the information that the driver is in a poor state of health and that an accident is to be expected or that assistance should be provided for the driver, for example. Safety system 10 may thus transmit corresponding information to other road users, e.g., second vehicle 2 or stationary computer unit 14, by appropriate data transmission with the aid of communication device 5. Second vehicle 2 has a second communication device 11 to receive data. In addition, safety system 10 may also transmit corresponding information and data to a hospital 12. Hospital 12 has a third communication device 13 for receiving and transmitting data. Third communication device 13 is connected to second computer unit 14. Second computer unit 14 is in turn connected to a second memory 15. In addition, a second input/output 16 is provided which is connected to second computer unit 14.

Safety system 10 may also be designed to be able to deliver acoustic or visual warning signals, for example, by operating a horn of the vehicle or by operating an emergency flasher of the vehicle. In addition, safety system 10 is also designed to start an automatic driving function of the vehicle. Thus at least partial functions of the operation of the vehicle are carried out by the automatic driving function and not by the driver. The automatic driving function may include automatic parking of the vehicle at the side of the road in particular. In addition, safety system 10 may be designed to at least limit or suppress certain functions of the vehicle. For example, the speed of the vehicle may be limited to a maximum value in the case of a certain state of health of the driver. Furthermore, however, the entire operation of the vehicle, in particular starting of the vehicle, may be suppressed in the case of a predefined state of health of the driver. Furthermore, with the aid of safety system 10, an E-call function may be carried out, in which the driver's state of health is transmitted to an appropriate place, in particular to the hospital. Communication device 5 may use a car-to-car data transmission system for transmitting information.

Reference values for the driver's state of health may be saved in memory 6 of vehicle 1 or in a mobile memory 9. Furthermore, with the aid of communication device 5, data about the driver's state of health, in particular reference values, may be received from external second computer unit 14. The Internet, WLAN or LTE, for example, may be used for data transmission.

Furthermore, instead of or in addition to communication device 5, a mobile communication device may be used for data exchange, in particular a mobile telephone connected to computer unit 4.

In addition, data about the driver's state of health detected by measuring unit 8 may be transmitted to external second computer unit 14 with the aid of communication device 5 and third communication device 13. Data are saved by second computer unit 14 in second memory 15. This offers the advantage that a more accurate analysis of the detected data is possible with the aid of external second computer unit 14 by operation of second input/output 16. Furthermore, for a precise evaluation of the driver's state of health, more and more accurate data and a chronological course of the driver's state of health may be made available in medical records in a hospital 12, for example.

Furthermore, in one exemplary embodiment, measuring unit 8 may be triggered externally via the data link with the aid of third communication device 13 and communication device 5 in order to carry out certain measurements on the driver. Thus a telemedicine system may be used, so that a physician is able to examine the driver's state of health in greater detail via a data link by specifying individual measurements.

Depending on the specific, exemplary embodiment selected, measuring methods which are automatically initiated on detection of a measured value by measuring unit 8 may also be saved in memory 6 of vehicle 1. For example, a choice may be offered to the driver via a corresponding output of whether he/she carries out additional measurements with the aid of measuring unit 8 or whether he/she stops the operation of the vehicle with the aid of measuring unit 8. Measuring unit 8 may also be supported by systems for fatigue or drowsiness recognition and alcohol detection.

One advantage of the system described here is that a possible serious health problem of the driver is detected early, resulting in impairment of the driver's ability to drive. After this state has been detected or after a future occurrence of this state has been detected, operation of the vehicle may be restricted, in particular prevented, and a physician or an emergency medical service may be informed.

Depending on the specific, exemplary embodiment selected, second computer unit 14 and second memory 15 may be part of a cloud system, which may be accessed via the Internet. Furthermore, vehicle 1 may have a navigation system 17, which is used for trip planning. Navigation system 17 may also request information about current traffic data, e.g., traffic jams, accidents, construction sites, etc., from external databases via communication device 5. In evaluating the driver's state of health, for example, the road ahead, i.e., the duration of the trip and the presence of traffic jams, accidents or construction sites may also be taken into account in considering the function to be triggered by safety system 10. For example, in the case of a short remaining travel time of five minutes, for example, to the destination, it may not be necessary to stop or limit operation of the vehicle if the driver's state of health is only mildly impaired. Furthermore, the current position of the vehicle, which is known from navigation system 17, which has a positioning unit, may also be transmitted, preferably during transmission of the data about the driver's state of health to hospital 12.

Furthermore, depending on the driver's prevailing state of health, a less tiring driving route may be selected by the navigation system. For example, if the driver's state of health is impaired, sections of highway or sections of roads having multiple traffic lanes, where the average driving speed is high, and/or where traffic density is high may be avoided.

Figure 2:
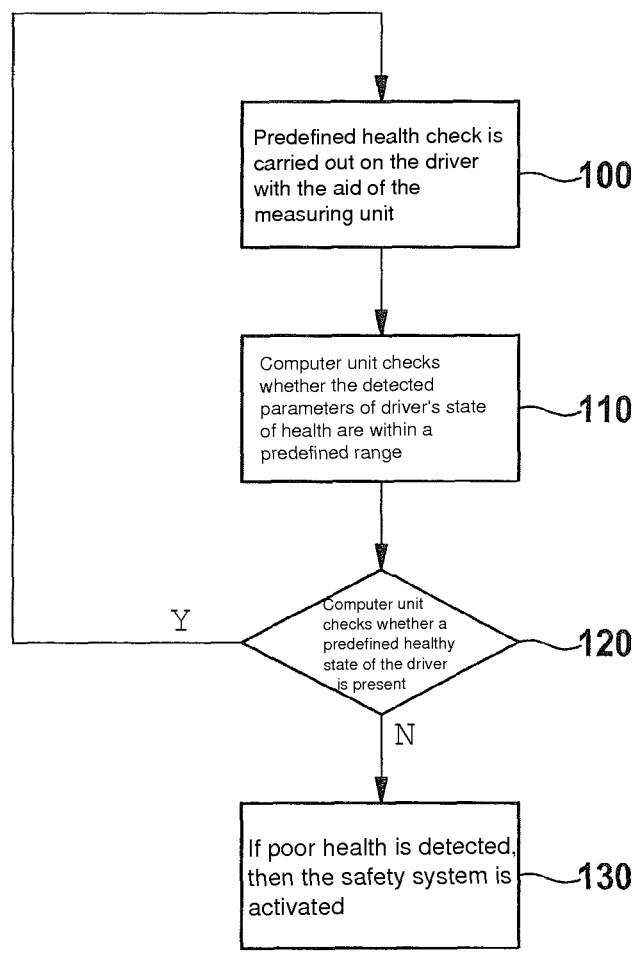
FIG. 2 shows a schematic program sequence for carrying out the method.

FIG. 2 shows a schematic program sequence for carrying out a method for operating a vehicle. At program point 100, a predefined health check is carried out on the driver with the aid of measuring unit 8, preferably before starting the vehicle. Corresponding programs and corresponding parameters for carrying out the health check are saved in memory 6 or in mobile memory 9 or are provided from external second memory 15 with the aid of communication device 5.

The present invention therefore relates to the problem of protecting the driver and other road users from consequences of health problems of the driver, among other things.

For this purpose, the driver's state of health is checked before starting the vehicle and/or is checked regularly during operation of the vehicle, in particular in the case of chronically ill people. In this check, predefined data about the driver's state of health are taken into account. In a simple, exemplary embodiment, a single reference value is used to evaluate the driver's state of health. Furthermore, data from the driver's last check may preferably also be used. The last check may be, for example, a check on the driver's state of health in the morning, carried out at home. The data from the morning health check are made available to the vehicle via a mobile memory or a data transmission, for example. The check may yield the result that the driver does not have any health problems or that the driver has a predefined poor state of health.

At subsequent program point 110, computer unit 4 checks on whether the detected parameters of the driver's state of health are within a predefined range, which is defined by saved or supplied reference values. In the simplest case, measured value is compared with a reference value. If the measured value exceeds the reference value, then this indicates a poor state of health. Value ranges may also be used for the comparison. At subsequent program point 120, computer unit 4 checks on whether a predefined healthy state of the driver is present. If this is the case, then the functionality of the vehicle, in particular the options of operating the vehicle by the driver, is not limited and the program branches off to program point 100. Therefore, the vehicle may be started and operated.

If computer unit 4 detects at program point 120 that a predefined poor state of health of the driver is present, then the program branches off to program point 130. Safety system 10 is activated at program point 130. Safety system 10 then carries out one of the following functions, depending on the predefined values and parameters:

outputting a general warning to the driver and to the passenger;
 outputting a warning signal to other road users, in particular by honking or flashing lights;
 informing other road users with the aid of communication device 5 about the existence of a critical state of health and a possible accident;
 transmitting the driver's state of health to a hospital or physician with the aid of communication device 5;
 starting an automatic driving function which at least partially takes over the operation of the vehicle;
 starting automatic parking of the vehicle;
 limiting a function of the vehicle, for example, predefining a maximum speed;
 suppressing the operation of the vehicle, etc.

The predefined functions activated by safety system 10 are defined as a function of the driver's state of health, for example. If there is a slight impairment in the driver's state of health, the occurrence of an accident is relatively unlikely, so that a limitation of the speed of the vehicle, for example, is sufficient. The more serious the impairment of the driver's state of health, the greater is the intervention into the operability and operation of the vehicle by the safety system. For example, if a heart attack occurs, an automatic driving function of the vehicle is activated immediately and the vehicle is safely parked on the side of the road. Appropriate tables and calculation methods are predefined for a correlation between the possible functions of safety system 10 and the prevailing state of health and the physiological measured values. These may be saved in memory 6 or in mobile memory 9, or they may be obtained from second computer unit 14 via communication device 5.

Depending on the specific, exemplary embodiment selected, the check on the state of health may also be carried out by external second computer 14. Furthermore, external second computer unit 14 may transmit the state of health thereby ascertained to vehicle 1. Furthermore, in another exemplary embodiment, second computer unit 14 may also transmit an instruction to safety system 10 and to the vehicle depending on the detected state of health in order to carry out a predefined intervention into the operability of the vehicle. A type of remote control of vehicle 1, which depends on the driver's state of health, may thus be implemented.

What is claimed is:

1. A method for operating a vehicle, comprising:
 checking a state of health of a driver at least one of during operation of the vehicle and when the vehicle is started; and
 starting a safety program for operating the vehicle when a predefined state of health is detected, wherein the safety program: (i) includes starting at least one of an automatic driving function and automatic parking of the vehicle, (ii) includes one of limiting a function of the vehicle, limiting a maximum speed of the vehicle, and suppressing operation of the vehicle, and (iii) starts different functions, depending on the driver's state of health.

2. The method according to claim 1, wherein the driver's state of health is checked at predefined, regular time intervals during operation of the vehicle, and the safety program is started when the predefined state of health is detected.

3. The method according to claim 1, wherein the safety program includes an output of a warning signal.

4. The method according to claim 1, wherein at least one of a reference value and a result of a previous check is taken into account for an evaluation of the state of health.

5. The method according to claim 1, further comprising:
 saving a result of the checking of the state of health in a memory in the vehicle or in an external memory.

6. The method according to claim 5, wherein a mobile memory in the vehicle is used as the memory.

7. The method according to claim 4, wherein the reference value is obtained from an external database.

8. The method according to claim 1, further comprising:
 transmitting corresponding information to at least one of other road users and other vehicles after detection of the predefined state of health.

9. A system for checking on a state of health of a driver of a vehicle, wherein the system is configured to carry out a method, the method comprising:
 checking the state of health of the driver at least one of during operation of the vehicle and when the vehicle is started; and
 starting a safety program for operating the vehicle when a predefined state of health is detected, wherein the safety program: (i) includes starting at least one of an automatic driving function and automatic parking of the vehicle, (ii) includes one of limiting a function of the vehicle, limiting a maximum speed of the vehicle, and suppressing operation of the vehicle, and (iii) starts different functions, depending on the driver's state of health.

10. A mobile device, configured to keep at least one of data and a reference value ready, for checking a state of health of a driver of a vehicle at least one of during operation of the vehicle and when the vehicle is started, and to exchange the at least one of data and the reference value with a system of the vehicle, wherein the safety program: (i) includes starting at least one of an automatic driving function and automatic parking of the vehicle, (ii) includes one of limiting a function of the vehicle, limiting a maximum speed of the vehicle, and suppressing operation of the vehicle, and (iii) starts different functions, depending on the driver's state of health.

11. A non-transitory, computer-readable medium having program code stored thereon, which, when executed by a computer, performs a method, the method comprising:
 checking a state of health of a driver of a vehicle at least one of during operation of the vehicle and when the vehicle is started; and
 starting a safety program for operating the vehicle when a predefined state of health is detected, wherein the safety program: (i) includes starting at least one of an automatic driving function and automatic parking of the vehicle (ii) includes one of limiting a function of the vehicle, limiting a maximum speed of the vehicle, and suppressing operation of the vehicle, and (iii) starts different functions, depending on the driver's state of health.

12. The method according to claim 1, further comprising:
 checking the state of health of the driver at least once during a running operation of the vehicle in addition to checking when the vehicle is started.

13. The system according to claim 9, the method further comprising:
 checking the state of health of the driver at least once during a running operation of the vehicle in addition to checking when the vehicle is started.

14. The mobile device according to claim 10, wherein the state of health of the driver of the vehicle is further checked at least once during a running operation of the vehicle in addition to checking when the vehicle is started.

15. The non-transitory, computer-readable medium according to claim 11, the method further comprising:
 checking the state of health of the driver at least once during a running operation of the vehicle in addition to checking when the vehicle is started.

16. The non-transitory, computer-readable medium according to claim 11, wherein the checking is triggered by a device external to the vehicle.

17. The system according to claim 9, wherein the checking is triggered by a device external to the vehicle.

18. The mobile device according to claim 10, wherein the checking is triggered by a device external to the vehicle.

19. The method according to claim 1, wherein the checking is triggered by a device external to the vehicle.

\* \* \* \* \*